United States Patent
Sawamura et al.

(10) Patent No.: US 7,386,422 B2
(45) Date of Patent: Jun. 10, 2008

(54) EXPERIMENT ANALYSIS SYSTEM

(75) Inventors: Masayuki Sawamura, Tokyo (JP); Ryouta Etou, Tokyo (JP); Takashi Shimizu, Tokyo (JP); Allan Minn, Alameda, CA (US)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 127 days.

(21) Appl. No.: 11/318,456

(22) Filed: Dec. 28, 2005

(65) Prior Publication Data
US 2007/0150207 A1 Jun. 28, 2007

(51) Int. Cl.
*G06F 19/00* (2006.01)
(52) U.S. Cl. .................................................. 702/183
(58) Field of Classification Search ................ 702/183, 702/58, 63; 324/500; 700/292; 714/1
See application file for complete search history.

(56) References Cited

U.S. PATENT DOCUMENTS

2003/0003494 A1* 1/2003 Ogura et al. .................. 435/6
2006/0084103 A1* 4/2006 Yamasaki et al. ............. 435/6

OTHER PUBLICATIONS http://www.m-w.com/dictionary/reagent, p. 1.*

\* cited by examiner

*Primary Examiner*—Tung S Lau
(74) *Attorney, Agent, or Firm*—Reed Smith LLP; Stanley P. Fisher, Esq.; Juan Carlos A. Marquez, Esq.

(57) ABSTRACT

An experiment analysis system eliminates the need to enter sample information each time an analysis processing unit is activated. The experiment analysis system includes a measurement device for measuring the expression levels of a sample using a reagent, an experiment processing unit for processing measurement data transmitted from the measurement device and creating an experimental result file, and a plurality of analysis processing units for analyzing the experimental results based on the experimental result file. The experiment processing unit transmits the experimental result file, which includes measurement data, an ID code identifying one of the plurality of analysis processing units, and sample information regarding the sample, to the analysis processing unit.

10 Claims, 4 Drawing Sheets

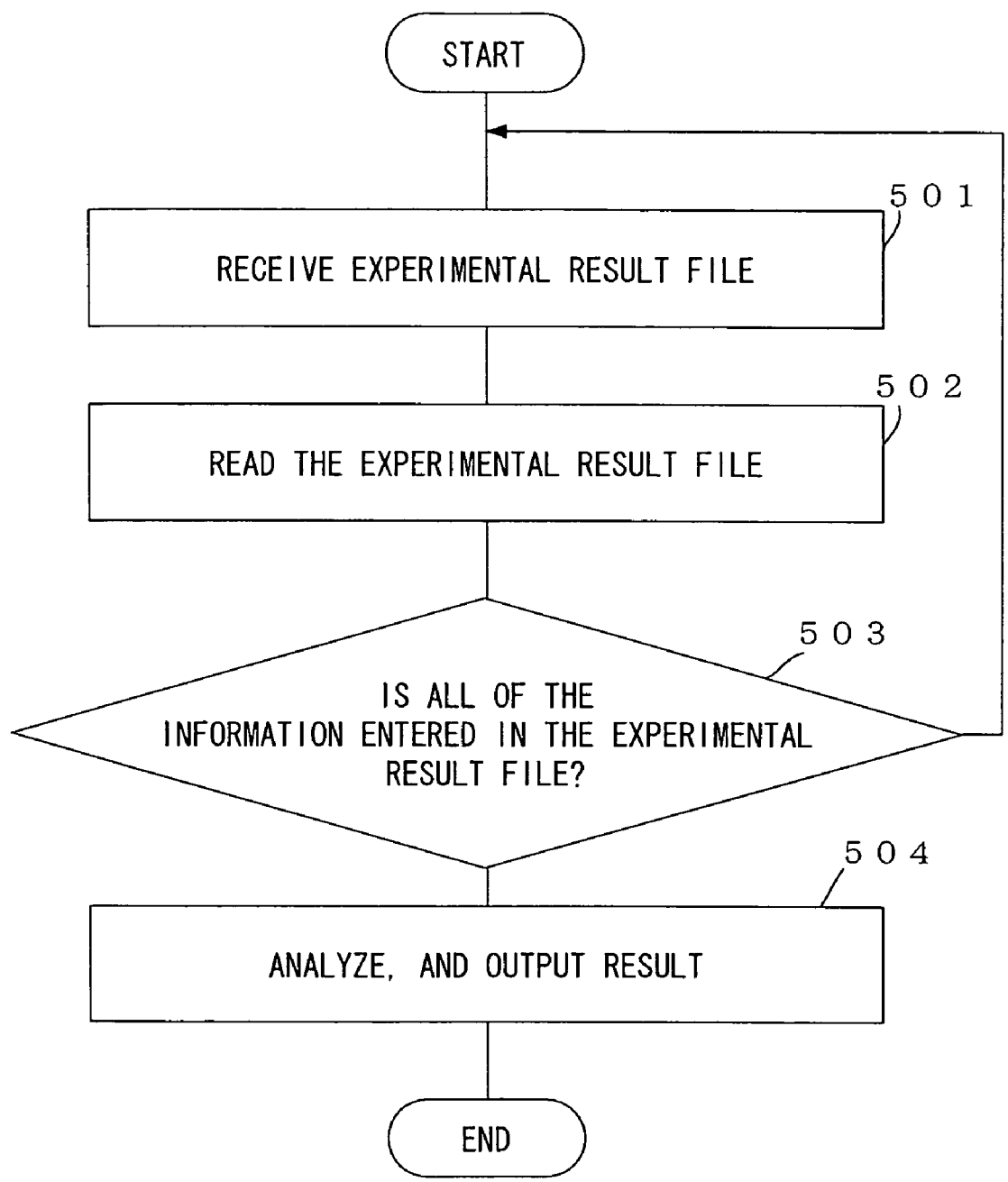

EXPERIMENT ANALYSIS SYSTEM

BACKGROUND OF THE INVENTION

1. Field of the Invention

The present invention relates to an experiment analysis system for measuring and analyzing expression levels of biomolecules, such as proteins or nucleic acid, in a sample, using a reagent.

2. Background Art

HLA type determination or protein concentration measurement and the like in bone marrow transplantation involves an experiment processing step for obtaining experimental results from measurement data, such as expression levels, outputted from measurement equipment, and an analysis step for analyzing the experimental results. In other words, such determination or measurement involves an experiment processing program for decoding measurement data, such as expression levels, and generating experimental results therefrom, and an analysis program for analyzing the experimental results. Normally, a plurality of analysis programs are prepared for a single experiment processing program, and an optimum analysis program for each experiment is selected. The experiment processing program and the analysis program are separately managed.

SUMMARY OF THE INVENTION

In conventional experiment analysis systems, measurement data alone is provided from the experiment processing step to the analysis step and no sample information is provided thereto. Thus, it has been necessary to enter sample information during the analysis step.

In a biological or biochemical experiment, experimental results might vary even when the same measurement equipment is used under the same experimental conditions. In such a case, different analysis programs are used. This requires that sample information be entered each time measurement data is entered into the analysis program. As a result, even when the sample information is identical, the same sample information needs to be re-entered if the analysis programs are different.

It is therefore an object of the invention to provide an experiment analysis system that does not require the entry of sample information each time an analysis processing unit is activated.

In accordance with the invention, an experiment analysis system includes: a measurement device for measuring the expression levels of a sample using a reagent; an experiment processing unit for processing measurement data transmitted from the measurement device and creating an experimental result file; and a plurality of analysis processing units for analyzing the experimental result based on the experimental result file. The experiment processing unit creates an experimental result file having measurement data, an ID code identifying one of the plurality of analysis processing units, and sample information regarding the sample, and transmits the experimental result file to the analysis processing unit.

In accordance with the invention, processes can be simplified because the need to enter sample information each time an analysis processing unit is activated is eliminated.

BRIEF DESCRIPTION OF THE DRAWINGS

FIG. 5 shows processes in the analysis processing unit of the experiment analysis system of the invention.

DESCRIPTION OF PREFERRED EMBODIMENTS

Figure 1:
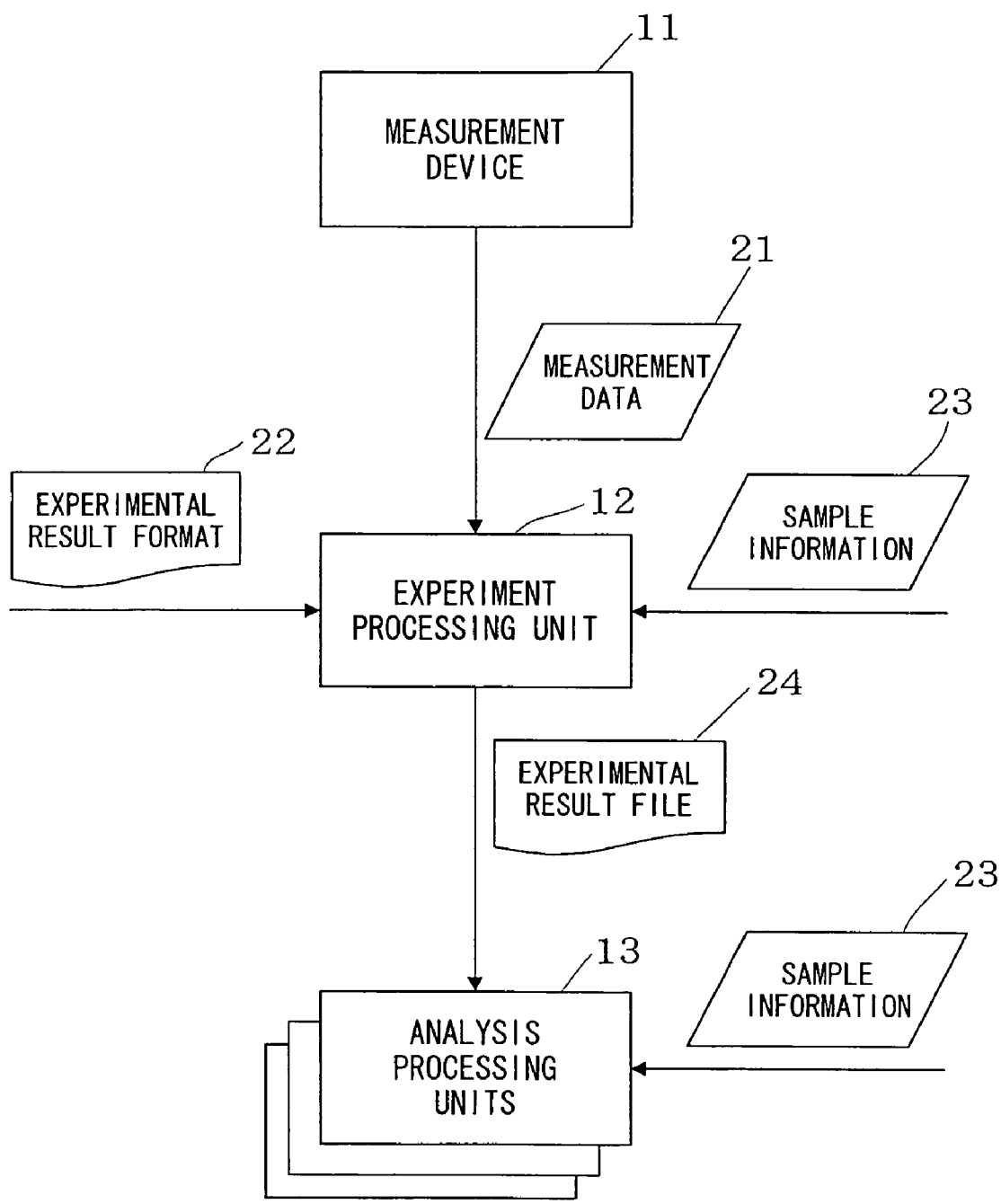
FIG. 1 shows an example of an experiment analysis system according to the invention.

An example of an experiment analysis system according to the invention will be described with reference to FIG. 1. The experiment analysis system in the present example includes a measurement device 11 for measuring expression levels of a sample using a reagent in a biological or biochemical experiment and the like, an experiment processing unit 12 for processing measurement data 21 transmitted from the measurement device 11 and creating an experimental result file 24, and a plurality of analysis processing units 13 for analyzing the experimental result based on the experimental result file 24. The measurement device 11 and the experiment processing unit 12 are used in all of the experiments, while only one of the plurality of analysis processing units 13 is used in an experiment. Which one of the analysis processing units 13 is used depends on the type of experiment and its contents, for example. However, once the type of experiment and its contents and the like are determined, one of the analysis processing units 13 that is to be used is automatically determined. Management of the measurement device 11 and experiment processing unit 12 and that of the analysis processing unit 13 are normally done separately.

The measurement device 11 sends measurement data 21 to the experiment processing unit 12. The measurement data 21 is an electrical signal produced by the measurement device 11 and is transmitted via a cable, for example. A variety of biochemical experiments are conducted using the measurement device 11, which generates expression levels and the like as measurement data.

A user enters sample information 23 into the experiment processing unit 12. The entry process may be performed using the analysis processing unit 13. In this case, the entered sample information is transmitted to the experiment processing unit 12. The operation of the experiment processing unit 12 and the analysis processing unit 13 will be described later.

The experiment processing unit 12 and the plurality of analysis processing units 13 may be caused to perform relevant processes using software.

Figure 2:
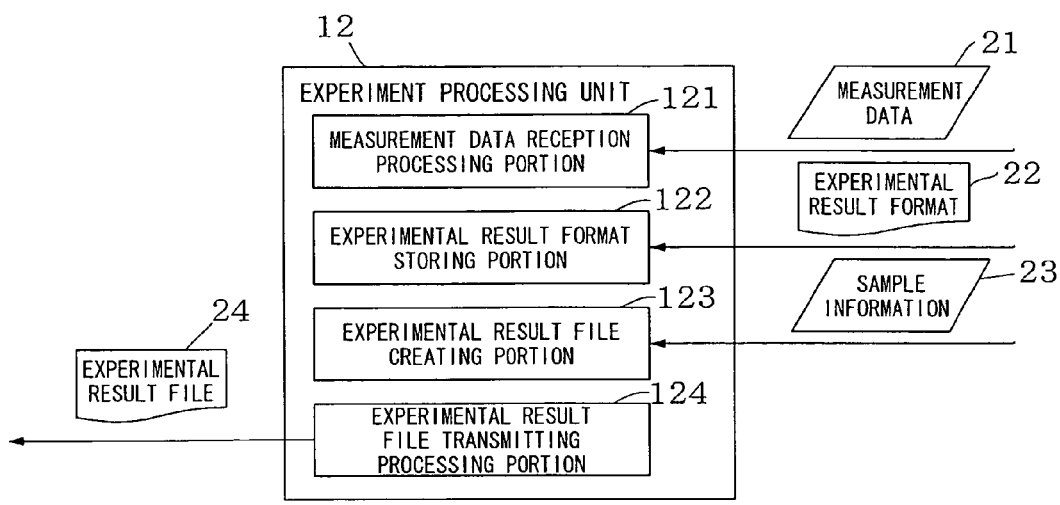
FIG. 2 shows an example of the structure of an experiment processing unit of the experiment analysis system of the invention.

The structure of the experiment processing unit 12 is described with reference to FIG. 2. The experiment processing unit 12 includes a measurement data reception processing portion 121 for receiving the measurement data 21 transmitted from the measurement device 11, an experimental result format storing portion 122 for storing an experimental result format 22 that is set by the user, an experimental result file creating portion 123 for creating an experimental result file 24 by entering sample information or the like in the experimental result format 22, and an experimental result file transmitting processing portion 124 for transmitting the experimental result file 24 to a predetermined analysis processing unit 13.

Figure 3:
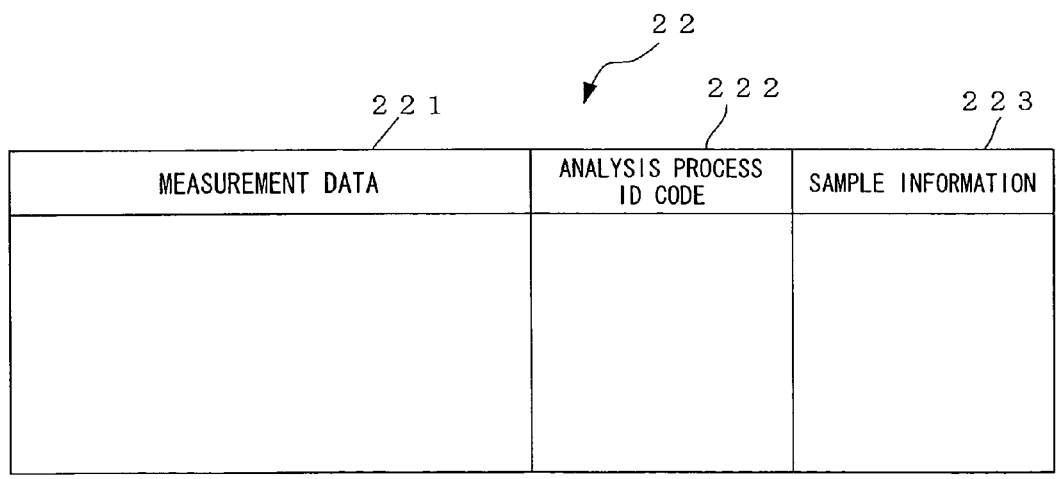
FIG. 3 shows an example of an experimental result format used in the experiment analysis system of the invention.

FIG. 3 shows an example of the experimental result format 22. In this example, the experimental result format 22 includes a measurement data area 221 in which measurement data is stored, an analysis process ID code area 222 for storing an ID code for the analysis processing unit (or an analysis processing program), and a sample information area 223 for storing sample information. The sample information includes the type of sample, number of samples, and the specification of a sample plate, for example. As mentioned above, one of the plurality of analysis processing units (analysis programs) is selected by the user and thus determined prior to the start of an experiment.

By storing the aforementioned data, code, information, and so on in each of areas in this experimental result format 22, an experimental result file 24 is created.

In the present example, when the sample information is identical throughout a plurality of experiments, an experimental result file is created by simply entering the measurement data and the ID code for the analysis processing unit (or analysis processing program) in the experimental result format 22. Thus, the processes in the experiment analysis step are simplified.

Figure 4:
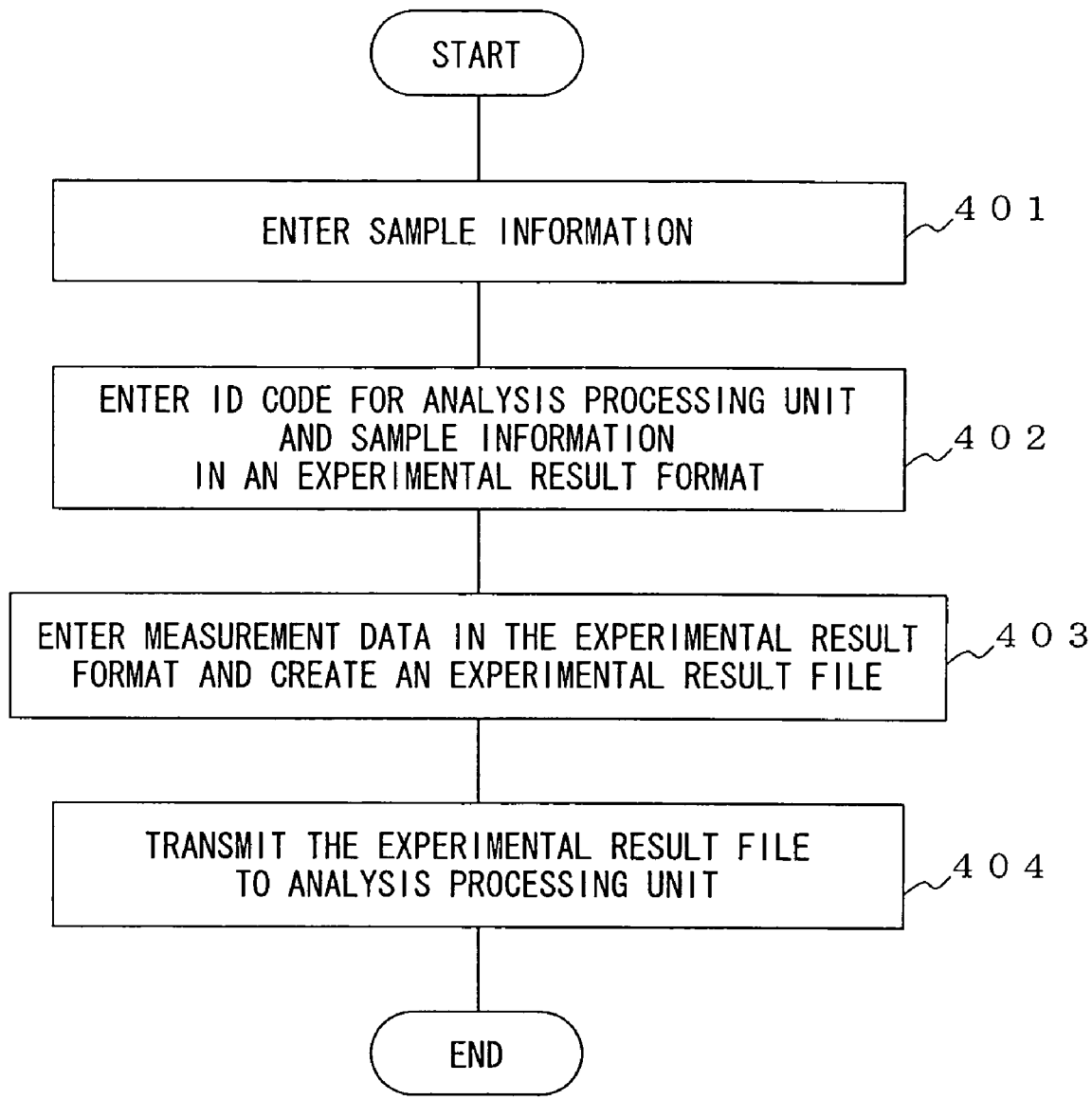
FIG. 4 shows processes in the experiment processing unit of the experiment analysis system of the invention.

The processes in the experiment processing unit 12 in accordance with the invention are described with reference to FIG. 4. At step 401, sample information is entered, either via the experiment processing unit 12, as mentioned above, or via the analysis processing unit 13. At step 402, the experimental result file creating portion 123 stores the ID code for the analysis processing unit (or analysis program) in the analysis process ID code area 222 of the experimental result format 22, and enters the sample information 23 in the sample information area 223. At step 403, the experimental result file creating portion 123 stores the measurement data 21 in the measurement data area 221 of the experimental result format 22. In this way, an experimental result file 24 is created. At step 404, the experimental result file transmitting processing portion 124 identifies the analysis processing unit 13 based on the analysis process ID code denoted in the analysis process ID code area 222 of the experimental result format 22. The experiment result file transmitting processing portion 124 then transmits the experimental result file 24 to the thus identified analysis processing unit 13.

The processes in the analysis processing unit 13 in accordance with the invention are described with reference to FIG. 5. At step 501, the analysis processing unit 13 receives the experimental result file 24 and then reads it at step 502. At step 503, the analysis processing unit 13 determines whether or not all of the required data is entered in the experimental result file. Specifically, it is determined whether or not the measurement data is stored in the measurement data area, whether or not the ID code for the analysis processing unit (analysis program) is stored in the analysis process ID code area, and whether or not sample information is stored in the sample information area. If all of the information is stored in the experimental result file, the routine proceeds to step 504. If not all of the information is stored in the experimental result file, the routine returns to step 501, where the experimental result file is received. At step 504, the analysis processing unit 13 carries out analysis and outputs an analysis result.

Thus, in the present example, the experimental result can be processed by one of a plurality of analysis processing units alone that corresponds to the sample information that is initially set.

While a preferred embodiment of the invention has been described, variations thereto will occur to those skilled in the art within the scope of the invention that is delineated by the following claims.

What is claimed is:

1. An experiment analysis system comprising:
a measurement device for measuring expression levels of a sample using a reagent;
an experiment processing unit for processing measurement data transmitted from the measurement device and creating an experimental result file; and
a plurality of analysis processing units for analyzing the experimental results based on the experimental result file,
wherein the experiment processing unit creates an experimental result file having the measurement data, an ID code identifying only a predetermined one of the plurality of analysis processing units, and sample information regarding the sample, and the experiment processing unit transmits the experimental result file to the predetermined analysis processing unit, and
wherein when the sample information is identical throughout a plurality of experiments, a different experimental result file is created for one of the experiments by entering the measurement data and the ID code for the analysis processing unit without re-entering the sample information.

2. An experiment analysis system comprising:
a measurement device for measuring expression levels of a sample using a reagent;
an experiment processing program or an experiment processor for processing measurement data transmitted from the measurement device and creating an experimental result file; and
a plurality of analysis processing programs or analysis processors for analyzing the experimental results based on the experimental result file,
wherein the experiment processing program or an experiment processor creates an experimental result file having the measurement data, an ID code identifying only a predetermined one of the plurality of analysis processing programs or analysis processors, and sample information regarding the sample, and the experiment processing program or an experiment processor transmits the experimental result file to the predetermined analysis processing program or analysis processor, and
when the sample information is identical throughout a plurality of experiments, a different experimental result file is created for one of the experiments by entering the measurement data and the ID code for the analysis processing program or analysis processor without re-entering the sample information.

3. The experiment analysis system according to claim 2, wherein the experiment processing program or an experiment processor comprises:
a measurement data reception processing portion for receiving the measurement data transmitted from the measurement device;
an experimental result format storing portion for storing an experimental result format set by a user;
an experimental result file creating portion for creating the experimental result file by entering the measurement data, the ID code, and the sample information in the experimental result format; and
an experimental result file transmitting processing portion for transmitting the experimental result file to the analysis processing program or analysis processor identified by the ID code.

4. The experiment analysis system according to claim 2, wherein the ID code and the sample information are entered in the experiment processing program or an experiment processor.

5. The experiment analysis system according to claim 2, wherein the ID code and the sample information are entered in the analysis processing program or analysis processor, via which they are transmitted to the experiment processing program or an experiment processor.

6. The experiment analysis system according to claim 2, wherein the experimental result format includes a measurement data area for storing measurement data, an analysis process ID number area for storing an ID code, and a sample information area for storing sample information.

7. The experiment analysis system according to claim 2, wherein processes in the experiment processor and processes in the analysis processor are carried out using software.

8. The experiment analysis system according to claim 2, wherein each of the analysis processing programs or analysis processors analyzes the experimental results differently.

9. The experiment analysis system according to claim 2, wherein the sample information includes types of samples, a number of samples, and a specification of a sample plate.

10. The experiment analysis system according to claim 8, wherein one of the analysis processing programs or analysis processors that is to be used is automatically determined based upon a type of experiment and relevant contents.

* * * * *